United States Patent [19]

Clémence et al.

[11] 4,299,831
[45] Nov. 10, 1981

[54] 2-TRIFLUOROMETHYL-3-QUINOLINE CARBOXAMIDES, ANALGESIC AND ANTI-INFLAMMATORY COMPOSITIONS AND METHODS EMPLOYING THEM

[75] Inventors: François Clémence, Paris; Roger Deraedt, Les Pavillons-sous-Bois; André Allais, Gagny; Odile Le Martret, Paris, all of France

[73] Assignee: Roussel Uclaf, Paris, France

[21] Appl. No.: 97,711

[22] Filed: Nov. 27, 1979

[30] Foreign Application Priority Data

Dec. 8, 1978 [FR] France ................ 78 34592

[51] Int. Cl.³ .................. A61K 31/47; C07D 215/56
[52] U.S. Cl. .................. 424/251; 424/258;
544/328; 544/331; 546/156
[58] Field of Search .............. 546/156; 424/258, 251;
544/328, 331

[56] References Cited

U.S. PATENT DOCUMENTS

3,992,540 11/1976 Clemence ........................ 424/258
4,044,138 8/1977 Curran et al. .................... 424/258
4,107,310 8/1978 Allais ............................. 546/156

OTHER PUBLICATIONS

Dey, et al., J. Het. Chem. vol. 2, No. 2, pp. 113–119 (1965).

*Primary Examiner*—Donald G. Daus
*Assistant Examiner*—Diana G. Rivers
*Attorney, Agent, or Firm*—Hammond & Littell, Weissenberger and Muserlian

[57] ABSTRACT

Novel 3-quinoline carboxamides of the formula

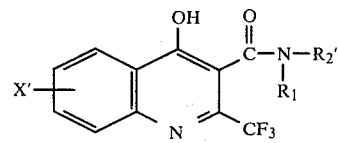

wherein X' is in the 5,6,7 or 8-position and is selected from the group consisting of hydrogen, halogen, straight or branched alkyl and alkoxy of 1 to 5 carbon atoms, —CF$_3$, —SCF$_3$ and —OCF$_3$, R$_1$ is selected from the group consisting of hydrogen and alkyl of 1 to 4 carbon atoms, R$_2$' is selected from the group consisting of thiazolyl, 4,5-dihydrothiazolyl, pyridinyl, oxazolyl, isoxazolyl, imidazolyl, pyrimidyl and tetrazolyl, all optionally substituted with alkyl of 1 to 4 carbon atoms and phenyl optionally substituted with at least one member of the group consisting of alkyl and alkoxy of 1 to 4 carbon atoms, —CF$_3$, —NO$_2$ and halogen and their non-toxic, pharmaceutically acceptable acid addition salts having analgesic and anti-inflammatory activity and novel intermediates and process for their preparation.

45 Claims, No Drawings

2-TRIFLUOROMETHYL-3-QUINOLINE CARBOXAMIDES, ANALGESIC AND ANTI-INFLAMMATORY COMPOSITIONS AND METHODS EMPLOYING THEM

STATE OF THE ART

Commonly assigned U.S. Pat. Nos. 3,992,540 and 4,107,310 and J. Het. Chem., Vol. 2, No. 2 (1965), Pennsylvania described related compounds.

OBJECTS OF THE INVENTION

It is an object of the invention to provide the novel 3-quinoline carboxamides of formula I′ and a process for their preparation and the novel intermediates formed therein.

It is another object of the invention to provide novel analgesic and anti-inflammatory compositions and to provide a novel method of relieving pain and inflammation in warm-blooded animals.

These and other objects and advantages of the invention will become obvious from the following detailed description.

THE INVENTION

The novel compounds of the invention are selected from the group consisting of 3-quinoline carboxamides of the formula

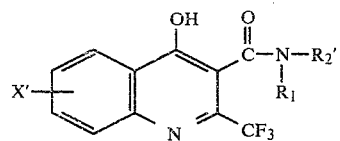

wherein X′ is in the 5,6,7 or 8-position and is selected from the group consisting of hydrogen, halogen, straight or branched alkyl and alkoxy of 1 to 5 carbon atoms, —CF$_3$, —SCF$_3$ and —OCF$_3$, R$_1$ is selected from the group consisting of hydrogen and alkyl of 1 to 4 carbon atoms, R$_2$′ is selected from the group consisting of thiazolyl, 4,5-dihydrothiazolyl, pyridinyl, oxazolyl, isoxazolyl, imidazolyl, pyrimidyl and tetrazolyl, all optionally substituted with alkyl of 1 to 4 carbon atoms and phenyl optionally substituted with at least one member of the group consisting of alkyl and alkoxy of 1 to 4 carbon atoms, —CF$_3$, —NO$_2$ and halogen and their non-toxic, pharmaceutically acceptable acid addition salts.

Among the preferred compounds of the invention are the compounds of the formula

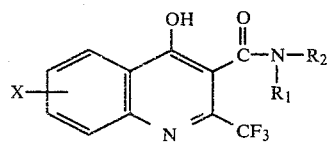

wherein R$_1$ has the above definition, X is in the 5,6,7 or 8-position and is selected from the group consisting of halogen, —CF$_3$, —SCF$_3$ and —OCF$_3$, R$_2$ is selected from the group consisting of thiazolyl, 4,5-dihydrothiazolyl, pyridinyl, oxazolyl, isoxazolyl, imidazolyl and pyrimidyl, all optionally substituted with alkyl of 1 to 4 carbon atoms and their non-toxic, pharmaceutically acceptable acid addition salts.

Examples of R$_1$ are hydrogen, methyl and ethyl. Examples of X or X′ are halogens such as chlorine, and alkyl and alkoxy of 1 to 5 carbon atoms such as methyl, ethyl, n-propyl, n-butyl, n-pentyl, isopropyl, isobutyl, methoxy, ethoxy and n-propoxy. When R$_2$ or R$_2$′ are substituted with an alkyl, it is preferably methyl or ethyl. When R$_2$′ is substituted phenyl, the preferred substituents are selected from the group consisting of methyl, ethyl, methoxy, ethoxy, —CF$_3$, —NO$_2$ and chlorine.

Examples of suitable acids for the non-toxic, pharmaceutically acceptable acid addition salts are inorganic acids such as hydrochloric acid, hydrobromic acid, sulfuric acid or phosphoric acid and alkylsulfonic acids such as methane sulfonic acid and arylsulfonic acids such as p-toluene sulfonic acid.

Among the preferred compounds of the invention of formula I′ are those wherein X′ is —CF$_3$ especially in the 8-position, those wherein R$_1$ is hydrogen, those wherein R$_2$′ is thiazolyl those wherein R$_2$′ is oxazolyl, those wherein R$_2$′ is isoxazolyl optionally substituted with alkyl of 1 to 4 carbon atoms, especially 5-methylisoxazolyl, those wherein R$_2$′ is pyrimidyl, those wherein R$_2$′ is imidazolyl optionally substituted with 1 to 4 alkyl carbon atoms, especially 1-methyl-1H-imidazolyl and those wherein R$_2$′ is tetrazolyl optionally substituted with alkyl of 1 to 4 carbon atoms and their nontoxic, pharmaceutically acceptable acid addition salts.

The novel process of the invention for the preparation of the compounds of formula I′ comprises reacting an acid of the formula

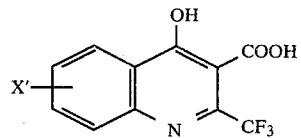

or a functional derivatives thereof wherein X′ has the above definition with a compound of the formula

wherein R$_1$ and R$_2$′ have the above definitions to obtain the corresponding compound of formula I′ which may be reacted with an acid to form the acid addition salt thereof.

In a preferred mode of the said process, the acid is used in the form of a functional derivative thereof such as its acid chloride, anhydride, mixed anhydride and a lower alkyl ester. The reaction is preferably effected in pyridine or in an inert organic solvent such as benzene, toluene or ethyl acetate in the presence of a basic agent, preferably triethylamine.

Another process of the invention for the preparation of a compound of formula II comprises reacting a compound of the formula

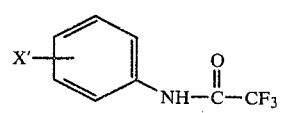

wherein X' has the above definition with a chlorination agent to obtain a compound of the formula

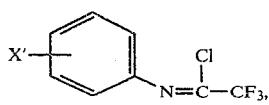   V reacting the latter with a malonate of the formula

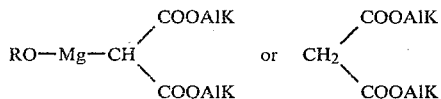

wherein AlK and R are individually alkyl of 1 to 8 carbon atoms in the presence of a strong base to form a compound of the formula

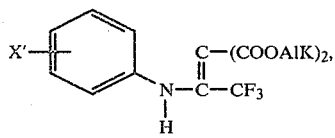   VI cyclizing the latter to form a compound of the formula

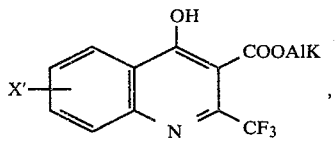   VII saponifying the latter to obtain the corresponding compound of formula II.

In a preferred mode of the process of the invention, the chlorination agent is preferably phosphorus pentachloride or a mixture of triphenylphosphine-carbon tetrachloride and the reaction is effected at 60°–120° C. The magnesium malonate derivative is preferred when R and AlK are individually methyl, ethyl or n-propyl and if the alkyl malonate is used, AlK is preferably ethyl and the reaction is effected in the presence of sodium hydride. The cyclization is preferably effected by heating at 150° to 250° C., for example. The saponification is preferably effected with sodium hydroxide or potassium hydroxide.

The starting compounds of formula IV are generally known compounds which can be prepared by the process described in Chem. Abs., Vol. 54, p. 4430i.

The novel intermediates of the invention are the compounds of formulae II, V, VI and VII.

The novel analgesic and anti-inflammatory compositions of the invention are comprised of an analgesically and anti-inflammatorily effective amount of at least one compound of formula I' and its non-toxic, pharmaceutically acceptable acid addition salts and an inert pharmaceutical carrier or excipient. The compositions may be in the form of tablets, dragees, gelules, granules, suppositories, injectable solutions or suspensions, pomades, creams, gels and aerosol preparations formed in the usual fashion.

Examples of suitable excipients are talc, arabic gum, lactose, starch, magnesium stearate, cacao butter, aqueous and non-aqueous vehicles, fatty bodies of animal or vegetable origin, paraffinic derivatives, glycols, diverse wetting agents, dispersants and emulsifiers and preservatives.

The compositions are useful for the treatment of muscular, articular or nervous pain, dental pain and migraines and the treatment of rhumatismatic affections.

The novel method of the invention for relieving pain and inflammation in warm-blooded animals, including humans, comprises administering to warm-blooded animals an analgesically and anti-inflammatorily effective amount of at least one compound of formula I' and its non-toxic, pharmaceutically acceptable acid addition salts. The compounds may be administered orally, rectally, parenterally or topically to the skin or mucous. The usual effective dose is dependent on the specific compound and the method of administration, and may be 0.4 to 40 mg/Kg per day in the adult by oral route.

In the following examples there are described several preferred embodiments to illustrate the invention. However, it should be understood that the invention is not intended to be limited to the specific embodiments.

EXAMPLE 1

2,8-bis-(trifluoromethyl)-4-hydroxy-N-(2-thiazolyl)-3-quinolinecarboxamide

STEP A:
2,2,2-trifluoro-N-(2-trifluoromethylphenyl)ethanimidoyl chloride

A mixture of 27.48 g of phosphorus pentachloride and 30.84 g of 2,2,2-trifluoro-N-(2-trifluoromethylphenyl)-acetamide was stirred at 80° C. for 4 hours and was then allowed to cool. The mixture was distilled under reduced pressure to obtain 15.2 g of 2,2,2-trifluoro-N-(2-trifluoromethylphenyl)ethanimidoyl chloride with a boiling point of 85° C. at 30 mm Hg and a refractive index of $n_D^{21} = 1.4297$.

STEP B: Ethyl 2-[2,2,2-trifluoro-1-(2-trifluoromethylphenylamine)-ethylidene]-propanedioate 4.8 g of sodium hydride as a 61% suspension in oil were added with stirring under nitrogen to 300 ml of toluene and then a solution of 20.8 g of ethyl malonate in 40 ml of toluene was added thereto dropwise at room temperature. The mixture was heated at 90° C. for 45 minutes and was then cooled to 20° C. A mixture of 25 g of the product of Step A in 30 ml of toluene was added to the reaction mixture and the mixture was refluxed for 4 hours and was cooled. The mixture was poured into an iced hydrochloric acid solution and was extracted with ether. The ether phase was washed with water, dried, filtered and evaporated to dryness. The 45 g of residue was chromatographed over silica gel to obtain 28.7 g of ethyl 2-[2,2,2-trifluoro-1-(2-trifluoromethylphenylamine)ethylidene]-propanedioate with a refractive index of $n_D^{21} = 1.4695$.

STEP C: Ethyl 2,8-bis-(trifluoromethyl)-4-hydroxy-3-quinoline-carboxylate 10 g of the product of Step B in a round flask with a distillation head was heated at 210° C. for about an hour and was then cooled to obtain 8.75 g of ethyl 2,8-bis-(trifluoromethyl)-4-hydroxy-3-quinoline-carboxylate melting at 68° C. which was used as is for the next step.

STEP D:
2,8-bis-(trifluoromethyl)-4-hydroxy-2-quinoline-carboxylic acid

A solution of 61.1 g of the product of Step C in 900 ml of ethanol and 300 ml of 36° Be sodium hydroxide solution was refluxed for 7 hours and the ethanol was evaporated under reduced pressure. The mixture was poured into water and the mixture was extracted with ether. The ether phase was washed with water and the combined aqueous phases were acidified with hydrochloric acid and were iced and vacuum filtered. The recovered crystals were washed and dried to obtain 53.4 g of 2,8-bis-(trifluoromethyl)-4-hydroxy-3-quinoline-carboxylic acid melting at 188° C.

STEP E:
2,8-bis-(trifluoromethyl)-4-hydroxy-3-quinoline-carboxylic acid chloride 9.6 ml of thionyl chloride were added with stirring to a suspension of 8.75 g of the product of Step D in 285 ml of benzene and the mixture was refluxed for 90 minutes. Then, the benzene and excess thionyl chloride was evaporated and the residue was taken up twice in anhydrous benzene to obtain 2,8-bis-(trifluoromethyl)-4-hydroxy-3-quinoline-carboxylic acid chloride which was used as is for the next step.

STEP F:
2,8-bis-(trifluoromethyl)-4-hydroxy-N-(2-thiazolyl)-3-quinolinecarboxamide A solution of 2.66 g of 2-amino-thiazole in 15 ml of pyridine was added to a suspension of 9.1 g of the product of Step E in 50 ml of pyridine and the mixture stood overnight at room temperature. The pyridine was evaporated under reduced pressure to obtain 15.9 g of residue which was dissolved in ethyl acetate. The solution was extracted with aqueous sodium bicarbonate solution and the organic phase was evaporated to dryness. the residue was empasted with methylene chloride and was crystallized from acetic acid to obtain 2.57 g of 2,8-bis-(trifluoromethyl)-4-hydroxy-N-(2-thiazolyl)-3-quinolinecarboxamide melting at 258° C.

EXAMPLE 2
2,8-bis-(trifluoromethyl)-4-hydroxy-N-(oxazol-2-yl)-3-quinoline-carboxamide A solution of 15.9 g of 2,8-bis-(trifluoromethyl)-4-hydroxy-3-quinoline-carboxylic acid chloride in 210 ml of ethyl acetate was added with stirring at 5°–8° C. under nitrogen to a solution of 3.57 g of 2-amino-oxazole and 4.3 g of triethylamine in 50 ml of ethyl acetate and after the temperature returned to room temperature, it stood overnight at that temperature. The mixture was vacuum filtered and the filtrate was washed and evaporated to dryness under reduced pressure. The 14.23 g of residue was triturated with 100 ml of N sodium hydroxide solution for 3 hours and was then diluted with 200 ml of water. The mixture was vacuum filtered and the filtrate was treated with activated carbon. The pH was adjusted to 1 by addition of N hydrochloric acid and the mixture was vacuum filtered. The recovered product was washed with water and dissolved in ethyl acetate. The solution was evaporated to dryness and the 8.77 g of product were crystallized twice from acetic acid to obtain 5.73 g (30.8% yield) of 2,8-bis-(trifluoromethyl)-4-hydroxy-N-(oxazol-2-yl)-3-quinoline-carboxamide melting at 258° C.

EXAMPLE 3
2,8-bis-(trifluoromethyl)-4-hydroxy-N-(5-methyl-isoxazol-3-yl)-3-quinoline-carboxamide Using the procedure of Example 2, 27.2 g of 2,8-bis-(trifluoromethyl)-4-hydroxy-3-quinoline-carboxylic acid chloride and 6.38 g of 3-amino-5-methyl-isoxazole were reacted to obtain 12.8 g of 2,8-bis-(trifluoromethyl)-4-hydroxy-N-(5-methyl-isoxazol-3-yl)-3-quinoline-carboxamide melting at 216° C.

EXAMPLE 4
2,8-bis-(trifluoromethyl)-4-hydroxy-N-(2-pyridinyl)-3-quinolinecarboxamide 13.4 g of 2,8-bis-(trifluoromethyl)-4-hydroxy-3-quinoline-carboxylic acid chloride suspended in 225 ml of benzene were added with stirring at 8° C. under nitrogen to a solution of 3.29 g of 2-amino-pyridine, 3.54 g of triethylamine and 70 ml of benzene and the temperature was allowed to rise to room temperature. The mixture was refluxed for one hour and was cooled and then 300 ml of water and 750 ml of ethyl acetate were added thereto. The mixture was filtered and the decanted organic phase was extracted with aqueous sodium bicarbonate solution and was washed. The organic phase was dried, filtered and evaporated to dryness to obtain 11.52 g of residue which was crystallized from acetic acid to obtain 5.77 g of 2,8-bis-(trifluoromethyl)-4-hydroxy-N-(2-pyridinyl)-3-quinolinecarboxamide melting at 236° C.

EXAMPLE 5
2,8-bis-(trifluoromethyl)-4-hydroxy-N-(1-methyl-1H-imidazol-2-yl)-3-quinolinecarboxamide Using the procedure of Example 1, 2,8-bis-(trifluoromethyl)-4-hydroxy-3-quinoline-carboxylic acid chloride and 2-amino-N-methyl-imidazole were reacted to obtain a 33.9% yield of 2,8-bis-(trifluoromethyl)-4-hydroxy-N-(1-methyl-1H-imidazol-2-yl-)-3-quinolinecarboxamide melting at 259° C.

EXAMPLE 6
2,8-bis-(trifluoromethyl)-4-hydroxy-N-(3-chlorophenyl)-3-quinoline carboxamide A solution of 4.083 g of m-chloroaniline, 9.71 g of triethylamine and 65 ml of ethyl acetate was poured over 15 minutes at 8° C.–10° C. into a solution of 11.96 g of 2,8-bis-(trifluoromethyl)-4-hydroxy-3-quinoline-carboxylic acid chloride in 130 ml of ethyl acetate with violent stirring and the temperature was allowed to return to room temperature. The mixture was refluxed for one hour and was cooled and vacuum filtered. The filtrate was washed with water, was dried and evaporated to dryness at 40° C. under reduced pressure to obtain 17.14 g of a triethylamine salt. The residue was dissolved in 2 N sodium hydroxide solution which was then heated to reflux and cooled to room temperature. The mixture was vacuum filtered and the recovered product was dissolved in water. The solution was adjusted to a pH of 1 by addition of 20% hydrochloric acid and the mixture was vacuum filtered. The recovered product was crystallized from benzene to obtain 7.599 g of 2,8-bis-(trifluoromethyl)-4-hydroxy-N-(3- chlorophenyl)-3-quinolinecarboxamide melting at 152° C.

EXAMPLE 7

2,8-bis-(trifluoromethyl)-4-hydroxy-N-(1H-tetrazol-5-yl)-3-quinolinecarboxamide 5.03 g of anhydrous 5-amino-tetrazole were suspended with stirring at 8° C. in 230 ml of ethyl acetate and a solution of 21.9 g of 2,8-bis-(trifluoromethyl)-4-hydroxy-3-quinoline-carboxylic acid chloride in 230 ml of ethyl acetate and a solution of 18 g of triethylamine in 180 ml of ethyl acetate were simultaneously added to the reaction mixture over 15 minutes. The mixture returned to room temperature and was refluxed for one hour and cooled. The mixture was vacuum filtered and the recovered product was dissolved in one liter of water. The filtrate wash waters were added to the solution and the pH was adjusted to 1 by addition of 20% hydrochloric acid. The mixture was vacuum filtered and the recovered product was dissolved in 50 ml of 2 N sodium hydroxide. 150 ml of water were added to the solution and the mixture was heated to reflux and cooled. The mixture was acidified with 100 ml of 20% hydrochloric acid and was vacuum filtered. The product was dried and crystallized from 250 ml of acetic acid to obtain 12.279 g of 2,8-bis-(trifluoromethyl)-4-hydroxy-N-(1H-tetrazol-5-yl)-3-quinolinecarboxamide melting at >260° C.

Analysis: $C_{13}H_6F_6N_6O_2$; molecular weight=392.22. Calculated: %C 39.81; %H 1.54; %F 29.06; %N 21.43; Found: %C 39.6; %H 1.6; %F 28.1; %N 22.0.

EXAMPLE 8

2,7-bis-(trifluoromethyl)-4-hydroxy-N-(2-thiazolyl)-3-quinolinecarboxamide

STEP A:
2,2,2-trifluoro-N-(3-trifluoromethylphenyl)-acetamide 80 g of m-trifluoromethylaniline were added at 40° C. over 25 minutes to 124.97 g of trifluoroacetic acid anhydride and the mixture was stirred at room temperature under an inert atmosphere for 2 hours. The mixture was evaporated to dryness under reduced pressure and the residue was taken up in methylene chloride. The organic phase was washed with water and aqueous potassium carbonate solution and was evaporated to dryness to obtain 121.8 g of residue. 1.5 g of the residue was crystallized from petroleum ether (b.p.=60°-80° C.) to obtain 1.38 g of 2,2,2-trifluoro-N-(3-trifluoromethylphenyl)-acetamide melting at 69° C.

STEP B:
2,2,2-trifluoro-N-(3-trifluoromethylphenyl)-ethanimidoyl chloride

An intimate mixture of 120.3 g of the product of Step A and 106.6 g of phosphorus pentachloride was heated at 80° C. under an inert atmosphere for 5 hours and phosphorus oxychloride was distilled at 25° C. at 40 mm Hg to obtain 31.44 g of 2,2,2-trifluoro-N-(3-trifluoromethylphenyl)-ethanimidoyl chloride with a boiling point of 75° C. at 30 mm Hg.

STEP C: Ethyl
2-[2,2,2-trifluoro-1-(3-trifluoromethylphenylamino)ethylidene]-propanedioate 0.86 g of sodium hydride as a 50% oil dispersion was washed with petroleum ether (b.p.=60°-80° C.) and was then suspended in 3.2 ml of dry dimethylformamide. A solution of 3.25 g of ethyl malonate in 3.3 ml of dimethylformamide was added at 17° C. under an inert atmosphere over 30 minutes to the said suspension and the mixture was stirred for one hour at 20° C. 4 g of the product of Step B were added at 18°-20° C. over 30 minutes to the mixture while keeping the temperature below 23° C. and the mixture was stirred at room temperature for one hour and was poured into 100 ml of ice water. The mixture was extracted with ether and the organic phase was washed with an aqueous saturated sodium chloride solution, was dried and evaporated to dryness. The residue was chromatographed over silica gel and was eluted with methylene chloride to obtain 3.00 g of purified ethyl 2-[2,2,2-trifluoro-1-(3-trifluoromethylphenylamino)-ethylidene]-propanedioate.

Analysis: $C_{16}H_{15}NF_6O_4$; molecular weight=399.291. Calculated: %C 48.13; %H 3.78; %F 28.54; %N 3.50; Found: %C 48.3; %H 3.7; %F 28.2; %N 3.4.

STEP D: Ethyl
2,7-bis-(trifluoromethyl)-4-hydroxy-3-quinoline-carboxylate 32.62 g of the product of Step C were heated at 210° C. at atmospheric pressure for 90 minutes and then for 15 minutes at 30 mm Hg. The mixture was cooled and 10 ml of petroleum ether were added thereto. The mixture was iced and vacuum filtered to obtain 24.5 g of residue melting at 123° C. which was crystallized from isopropanol to obtain ethyl 2,7-bis-(trifluoromethyl)-4-hydroxy-3-quinoline-carboxylate melting at 156° C.

STEP E:
2,7-bis-(trifluoromethyl)-4-hydroxy-3-quinolinecarboxylic acid

A mixture of 21.38 g of the product of Step D, 300 ml of ethanol and 60.5 ml of sodium hydroxide solution was refluxed with stirring for 7 hours and the ethanol was then distilled under reduced pressure at 40° C. The residue was taken up in about 300 ml of water and the pH was adjusted to 1 by addition of 20% hydrochloric acid. The mixture was vacuum filtered and the recovered product was washed with water and was taken up in 350 ml of ether. The organic phase was washed with water, dried and evaporated to dryness under reduced pressure to obtain 18.65 g of 2,7-bis-(trifluoromethyl)-4-hydroxy-3-quinoline-carboxylic acid melting at 240° C.

STEP F:
2,7-bis-(trifluoromethyl)-4-hydroxy-3-quinolinecarboxylic acid chloride 31.89 g of thionyl chloride were added to a suspension of 17.246 g of the product of Step E in 535 ml of anhydrous benzene and the mixture was refluxed for 105 minutes and was then evaporated to dryness under reduced pressure at 40° C. The residue was taken up in benzene and the solution was evaporated to dryness under the same conditions to obtain 18.62 g of 2,7-bis-(trifluoromethyl)-4-hydroxy-3-quinolinecarboxylic acid chloride.

STEP G:
2,7-bis-(trifluoromethyl)-4-hydroxy-N-(2-thiazolyl)-3-quinolinecarboxamide A solution of 5.37 g of 2-amino-thiazole, 16.27 g of triethylamine and 214 ml of ethyl acetate were added with stirring over 25 minutes at 7° C. to a solution of 18.62 g of the product of Step F in 320 ml of ethyl acetate, and after the temperature returned to room temperature, the mixture was refluxed for one hour and cooled. The mixture was vacuum filtered and the filtrate was washed with water, dried and evaporated to dryness under reduced pressure at 40° C. The 19.22 gm of residue which was the triethylamine salt of the acid was taken up in 180 ml of 2 N sodium hydroxide solution and the mixture was refluxed for 3–4 minutes and was cooled. The mixture was vacuum filtered and the pH of the filtrate was adjusted to 1 by addition of 20% hydrochloric acid. The mixture was vacuum filtered and the recovered product was crystallized from acetic acid to obtain 8.22 g of 2,7-bis-(trifluoromethyl)-4-hydroxy-N-(2-thiazolyl)-3-quinolinecarboxamide melting at 270° C.

EXAMPLE 9

2-trifluoromethyl-4-hydroxy-N-(2-thiazolyl)-3-quinolinecarboxamide

STEP A: 2,2,2-trifluoro-N-phenyl-acetamide

Using the procedure of Step A of Example 8, aniline was reacted to obtain 2,2,2-trifluoro-N-phenyl-acetamide melting at 85° C. which after crystallization from petroleum ether (b.p.=60°–80° C.) melted at 87° C.

STEP B: 2,2,2-trifluoro-N-phenyl-ethanimidoyl chloride 118 g of triphenylphosphine and 44 ml of carbon tetrachloride were added at 20° C. under an inert atmosphere to a solution of 72.7 g of the product of Step A in 770 ml of methylene chloride and the mixture was refluxed for 6 hours. The methylene chloride was evaporated under reduced pressure and the residue was chromatographed over silica gel. Elution with methylene chloride yielded 84.0 g of product which was distilled to obtain 56.1 g of 2,2,2-trifluoro-N-phenyl-ethanimidoyl chloride boiling at 70° C. at 20 mm Hg.

STEP C: Ethyl (1-phenylamino-2,2,2-trifluoroethylidene)propanedioate

A solution of 52.8 g of ethyl malonate in 40 ml of dimethylformamide was added at 20° C. over 20 minutes to a mixture of 12.8 g of sodium hydride in 140 ml of dimethylformamide and the mixture was stirred for 30 minutes and was then cooled to 5° C. 56 g of the product of Step B were added thereto over 45 minutes and the mixture was stirred for 3½ hours while the temperature returned to 20° C. The mixture was poured into 400 ml of iced N hydrochloric acid and was extracted with ether. The ether phase was washed with water until the wash water was neutral, dried and evaporated to dryness to obtain 98.0 g of ethyl(1-phenylamino-2,2,2-trifluoroethylidene)-propanedioate.

STEP D: Ethyl 2-trifluoromethyl-4-hydroxy-3-quinolinecarboxylate

Using the procedure of Step D of Example 8, 96.0 g of the product of Step C were reacted to obtain 40.2 g of ethyl 2-trifluoromethyl-4-hydroxy-3-quinoline-carboxylate melting at 192° C.

STEP E: 2-trifluoromethyl-4-hydroxy-3-quinoline-carboxylic acid

Using the procedure of Step E of Example 8, 30 g of the product of Step D were reacted to obtain without ether purification 26.3 g of 2-trifluoromethyl-4-hydroxy-3-quinoline-carboxylic acid melting at 262° C.

STEP F: 2-trifluoromethyl-4-hydroxy-3-quinoline-carboxylic acid chloride

Using the procedure of Step F of Example 8, 12.85 g of the product of Step E were reacted with a reflux of 2½ hours to obtain 2-trifluoromethyl-4-hydroxy-3-quinoline-carboxylic acid chloride.

STEP G: 2-trifluoromethyl-4-hydroxy-N-(2-thiazolyl)-3-quinoline-carboxamide 7.5 g of 2-amino-thiazole and 20 ml of pyridine were added to a solution of the product of Step F in 120 ml of anhydrous pyridine and the mixture was heated at 80°–85° C. for one hour. The mixture was stirred at room temperature for 16 hours and was then evaporated to dryness. The residue was triturated with 200 ml of water and was then vacuum filtered. The filter was washed and the combined wash water and filtrate were cooled in ice and acidified with concentrated hydrochloric acid. The mixture was vacuum filtered and the recovered product was washed with water and dried to obtain 13.7 g of 2-trifluoromethyl-4-hydroxy-N-(2-thiazolyl)-3-quinoline-carboxamide melting at >280° C.

EXAMPLE 10

2-trifluoromethyl-6-isopropyl-4-hydroxy-N-(2-thiazolyl)-3-quinoline carboxamide

STEP A: N-(4-isopropylphenyl)-2,2,2-trifluoro-acetamide

Using the procedure of Step A of Example 8, 65 g of p-isopropylaniline and 121 g of trifluoroacetic acid anhydride were reacted to obtain 109 g of N-(4-isopropylphenyl)-2,2,2-trifluoro-acetamide melting at 98° C.

STEP B: N-(4-isopropylphenyl)-2,2,2-trifluoro-ethanimidoyl chloride

Using the procedure of Step B of Example 9, 96.9 g of the product of Step A were reacted to obtain 74.55 g of N-(4-isopropylphenyl)-2,2,2-trifluoro-ethanimidoyl chloride boiling at 110° C. at 20 mm Hg.

STEP C: Ethyl 2-[2,2,2-trifluoro-1-(4-isopropylphenylamino)ethylidene]-propanedioate Using the procedure of Step C of Example 9, 74.5 g of the product of Step B were reacted to obtain 111.3 g of raw ethyl 2-[2,2,2-trifluoro-1-(4-isopropylphenylamino)ethylidene]-propanedioate which was used as is for the next step.

STEP D: Ethyl 2-trifluoromethyl-6-isopropyl-4-hydroxy-3-quinolinecarboxylate

Using the procedure of Step D of Example 9, 123.4 g of the raw product of Step C were reacted to obtain after washing with hexane 52.15 g of ethyl 2-trifluoromethyl-6-isopropyl-4-hydroxy-3-quinolinecarboxylate melting at 95° C.

STEP E:
2-trifluoromethyl-6-isopropyl-4-hydroxy-3-quinolinecarboxylic acid

Using the procedure of Step E of Example 9, 25 g of the product of Step D were reacted to obtain 22 g of 2-trifluoromethyl-6-isopropyl-4-hydroxy-3-quinolinecarboxylic acid melting at 206° C.

STEP F:
2-trifluoromethyl-6-isopropyl-4-hydroxy-3-quinlinecarboxylic acid chloride Using the procedure of Step F of Example 9, 20 g of the product of Step E were reacted to obtain 2-trifluoromethyl-6-isopropyl-4-hydroxy-3-quinoline-carboxylic acid chloride.

STEP G:
2-trifluoromethyl-6-isopropyl-4-hydroxy-N-(2-thiazolyl)-3-quinolinecarboxamide Using the procedure of Step F of Example 1, the product of Step F and 10 g of 2-amino-thiazole were reacted to obtain after crystallization from isopropanol 9.64 g of 2-trifluoromethyl-6-isopropyl-4-hydroxy-N-(2-thiazolyl)-3-quinolinecarboxamide melting at 262° C.

EXAMPLE 11
2-trifluoromethyl-6-methoxy-4-hydroxy-N-(2-thiazolyl)-3-quinolinecarboxamide

STEP A:
N-(3-methoxyphenyl)-2,2,2-trifluoroacetamide

Using the procedure of Step A of Example 8, 65 g of p-methoxyaniline and 120 g of trifluoroacetic acid anhydride were reacted to obtain 113 g of N-(3-methoxyphenyl)-2,2,2-trifluoroacetamide melting at 115° C.

STEP B:
N-(3-methoxyphenyl)-2,2,2-trifluoro-ethanimidoyl chloride

Using the procedure of Step B of Example 9, 62 g of the product of Step A were reacted to obtain 40 g of N-(3-methoxyphenyl)-2,2,2-trifluoro-ethanimidolyl chloride boiling at 108° C. at 20 mm Hg.

STEP C: Ethyl 2-[2,2,2-trifluoro-(3-methoxyphenylamino)ethylidene]-propanedioate Using the procedure of Step C of Example 9, 6 g of the product of Step B were reacted to obtain 5 g of raw ethyl 2-[2,2,2-trifluoro-1-(3-methoxyphenylamino)-ethylidene]-propanedioate which was used as is for the next step.

STEP D: Ethyl 2-trifluoromethyl-6-methoxy-4-hydroxy-3-quinolinecarboxylate

Using the procedure of Step D of Example 9, 4.5 g of the product of Step C were reacted to obtain 3.36 g of ethyl 2-trifluoromethyl-6-methoxy-4-hydroxy-3-quinolinecarboxylate melting at 184° C.

STEP E:
2-trifluoromethyl-6-methoxy-4-hydroxy-3-quinoline carboxylic acid

Using the procedure of Step E of Example 9, 2.85 g of the product of Step D were reacted to obtain 2.50 g of 2-trifluoromethyl-6-methoxy-4-hydroxy-3-quinoline carboxylic acid melting at 256° C.

STEP F:
2-trifluoromethyl-6-methoxy-4-hydroxy-3-quinolinecarboxylic acid chloride Using the procedure of Step F of Example 9, 2 g of the product of Step E were reacted to obtain 2-trifluoromethyl-6-methoxy-4-hydroxy-3-quinoline carboxylic acid chloride.

STEP G:
2-trifluoromethyl-6-methoxy-4-hydroxy-N-(2-thiazolyl)-3-quinolinecarboxamide Using the procedure of Step F of Example 1, the product of Step F and 1.05 g of 2-amino-thiazole were reacted to obtain after crystallization from ethanol 1.6 g of 2-trifluoromethyl-6-methoxy-4-hydroxy-N-(2-thiazolyl)-3-quinolinecarboxamide melting at >270° C.

EXAMPLE 12

Tablets were prepared from 50 mg of the product of Example 1 and sufficient excipient of lactose, starch, talc and magnesium stearate for a final tablet weight of 350 mg.

PHARMACOLOGICAL DATA

A. Analgesic Activity

The test was based on that of Koster et al [Fed. Proc., Vol. 1B (1959), p. 412] in which mice received an intraperitoneal injection of acetic acid to provoke repeated stretching and twisting movements which persist for more than 6 hours. An analgesic prevents or reduces this syndrome which is considered to be an exteriorization of a diffuse abdominal pain. A 1% solution of acetic acid in water was used and the dose relieving the syndrome under these conditions was 0.1 mg/g or 100 mg/kg of acetic acid.

The test compound was orally administered to the mice 30 minutes before the acetic acid injection and the mice had been fasting for the previous 24 hours. The stretching were counted for each mouse for a 15 minute observation period after the acetic acid injection and the dose which diminished the number of stretchings by 50% as compared to the controls ($DA_{50}$) was 0.55 mg/kg for the compound of Example 1.

B. Anti-inflammatory Activity

The anti-inflammatory activity was determined by the arthritis test provoked by carraghenin in male rats weighing about 130 to 150 g which received 0.05 ml of sterile suspension of 1% carraghenin into the tibiotarisen articulation of the rear paw. Simultaneously the test product in a suspension in 0.25% carboxymethyl cellulose and 0.02% of Tween was orally administered. The volume of the paw was measured before the test and then 2,4,6,8 and 24 hours later. The intensity of inflammation was maximum at 4 to 6 hours after the injection of carraghenin and the difference in paw volume of controls and treated animals were evidence of anti-inflammatory action. The $DA_{50}$ dose which is that which reduced the edema by 50% was 4 mg/kg for the product of Example 1.

Various modifications of the products and processes of the invention may be made without departing from the spirit or scope thereof and it is to be understood that the invention is intended to be limited only as defined in the appended claims.

We claim:

1. A compound selected from the group consisting of 3-quinoline carboxamides of the formula

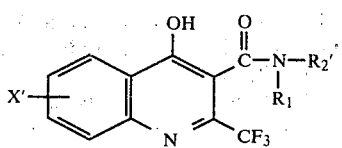

wherein X' is in the 5,6,7 or 8-position and is selected from the group consisting of hydrogen, halogen, straight or branched alkyl and alkoxy of 1 to 5 carbon atoms, —CF$_3$, —SCF$_3$ and —OCF$_3$, R$_1$ is selected from the group consisting of hydrogen and alkyl of 1 to 4 carbon atoms, R$_2'$ is selected from the group consisting of thiazolyl, 4,5-dihydrothiazolyl, pyridinyl, oxazolyl, isoxazolyl, imidazolyl, pyrimidyl and tetrazolyl, all optionally substituted with alkyl of 1 to 4 carbon atoms and their non-toxic, pharmaceutically acceptable acid addition salts.

2. A compound of claim 1 wherein X' is selected from the group consisting of halogen, —CF$_3$, —SCF$_3$ and —OCF$_3$ and R$_2'$ is selected from the group consisting of thiazolyl, 4,5-dihydrothiazolyl, pyridinyl, oxazolyl, isoxazolyl, imidazolyl and pyrimidyl, all optionally substituted with alkyl of 1 to 4 carbon atoms.

3. A compound of claim 1 wherein X' is —CF$_3$.
4. A compound of claim 1 wherein X' is 8—CF$_3$.
5. A compound of claim 1 wherein R$_1$ is hydrogen.
6. A compound of claim 1 wherein R$_2'$ is thiazolyl.
7. A compound of claim 1 wherein R$_2'$ is oxazolyl.
8. A compound of claim 1 wherein R$_2'$ is isoxazolyl optionally substituted with alkyl of 1 to 4 carbon atoms.
9. A compound of claim 8 wherein R$_2'$ is 5-methylisoxazolyl.
10. A compound of claim 1 wherein R$_2'$ is pyrimidyl.
11. A compound of claim 1 wherein R$_2'$ is imidazolyl optionally substituted with alkyl of 1 to 4 carbon atoms.
12. A compound of claim 11 wherein R$_2'$ is 1-methyl-1H-imidazolyl.
13. A compound of claim 1 wherein R$_2'$ is tetrazolyl optionally substituted with alkyl of 1 to 4 carbon atoms.
14. A compound of claim 1 selected from the group consisting of 2,8-bis-(trifluoromethyl)-4-hydroxy-N-(oxazol-2-yl)-3-quinoline-carboxamide, 2,8-bis-(trifluoromethyl)-4-hydroxy-N-(5-methyl-isoxazol-3-yl)-3-quinoline-carboxamide 2,8-bis-(trifluoromethyl)-4-hydroxy-N-(2-pyridinyl)-3-quinoline-carboxamide, 2,8-bis-(trifluoromethyl)-4-hydroxy-N-(1-methyl-1H-imidazol-2-yl)-3-quinoline-carboxamide 2,8-bis-(trifluoromethyl)-4-hydroxy-N-(1H-tetrazol-5-yl)-3-quinoline-carboxamide, 2,7-bis-(trifluoromethyl)-4-hydroxy-N-(2-thiazolyl)-3-quinoline-carboxamide, 2-trifluoromethyl-4-hydroxy-N-(2-thiazolyl)-3-quinoline-carboxamide, 2-trifluoromethyl-6-isopropyl-4-hydroxy-N-(2-thiazolyl)-3-quinoline-carboxamide, 2-trifluoromethyl-6-methoxy-4-hydroxy-N-(2-thiazolyl)-3-quinoline-carboxamide and their non-toxic, pharmaceutically acceptable acid addition salts.

15. A compound of claim 1 which is the 2,8-bis-(trifluoromethyl)-4-hydroxy-N-(2-thiazolyl)-3-quinoline carboxamide.

16. An anti-inflammatory and analgesic composition comprising an analgesically and anti-inflammatorily effective amount of at least one compound of claim 1 and an excipient.

17. A composition of claim 16 wherein X' is selected from the group consisting of halogen, —CF$_3$, —SCF$_3$ and —OCF$_3$ and R$_2'$ is selected from the group consisting of thiazolyl, 4,5-dihydrothiazolyl, pyridinyl, oxazolyl, isoxazolyl, imidazolyl and pyrimidyl, all optionally substituted with alkyl of 1 to 4 carbon atoms.

18. A composition of claim 16 wherein X' is —CF$_3$.
19. A composition of claim 16 wherein X' is 8—CF$_3$.
20. A composition of claim 16 wherein R$_1$ is hydrogen.
21. A composition of claim 16 wherein R$_2'$ is thiazolyl.
22. A composition of claim 16 wherein R$_2'$ is oxazolyl.
23. A composition of claim 16 wherein R$_2'$ is isoxazolyl optionally substituted with alkyl of 1 to 4 carbon atoms.
24. A composition of claim 16 wherein R$_2'$ is 5-methyl-isoxazolyl.
25. A composition of claim 16 wherein R$_2'$ is pyrimidyl.
26. A composition of claim 16 wherein R$_2'$ is imidazolyl optionally sbustituted with alkyl of 1 to 4 carbon atoms.
27. A composition of claim 16 wherein R$_2'$ is 1-methyl-1H-imidazolyl.
28. A composition of claim 16 wherein R$_2'$ is tetrazolyl optionally substituted with alkyl of 1 to 4 carbon atoms.
29. A composition of claim 16 selected from the group consisting of 2,8-bis-(trifluoromethyl)-4-hydroxy-N-(oxazol-2-yl)-3-quinoline-carboxamide, 2,8-bis-(trifluoromethyl)-4-hydroxy-N-(5-methyl-isoxazol-3-yl)-3-quinoline-carboxamide, 2,8-bis-(trifluoromethyl)-4-hydroxy-N-(2-pyridinyl)-3-quinoline-carboxamide, 2,8-bis-(trifluoromethyl)-4-hydroxy-N-(1-methyl-1H-imidazol-2-yl)-3-quinoline-carboxamide, 2,8-bis-(trifluoromethyl)-4-hydroxy-N-(1H-tetrazol-5-yl)-3-quinoline-carboxamide, 2,7-bis-(trifluoromethyl)-4-hydroxy-N-(2-thiazolyl)-3-quinoline-carboxamide, 2-trifluoromethyl-4-hydroxy-N-(2-thiazolyl)-3-quinoline-carboxamide, 2-trifluoromethyl-6-isopropyl-4-hydroxy-N-(2-thiazolyl)-3-quinoline-carboxamide, 2-trifluoromethyl-6-methoxy-4-hydroxy-N-(2-thiazolyl)-3-quinoline-carboxamide and their non-toxic, pharmaceutically acceptable acid addition salts.

30. A composition of claim 16 comprising 2,8-bis-(trifluoromethyl)-4-hydroxy-N-(2-thiazolyl)-3-quinoline carboxamide.

31. A method of relieving pain and inflammation in warm-blooded animals comprising administering to warm-blooded animals an analgesically and anti-inflammatorily effective amount of at least one compound of claim 1.

32. The method of claim 31 wherein X' is selected from the group consisting of halogen, —CF$_3$, —SCF$_3$ and —OCF$_3$ and R$_2'$ is selected from the group consisting of thiazolyl, 4,5-dihydrothiazolyl, pyridinyl, oxazolyl, isoxazolyl, imidazolyl and pyrimidyl, all optionally substituted with alkyl of 1 to 4 carbon atoms.

33. The method of claim 31 wherein X' is —CF$_3$.
34. The method of claim 31 wherein X' is 8—CF$_3$.
35. The method of claim 31 wherein R$_1$ is hydrogen.
36. The method of claim 31 wherein R$_2'$ is thiazolyl.
37. The method of claim 31 wherein R$_2'$ is oxazolyl.

38. The method of claim 31 wherein $R_2'$ is isoxazolyl optionally substituted with alkyl of 1 to 4 carbon atoms.

39. The method of claim 31 wherein $R_2'$ is 5-methylisoxazolyl.

40. The method of claim 31 wherein $R_2'$ is pyrimidyl.

41. The method of claim 31 wherein $R_2'$ is imidazolyl optionally substituted with alkyl of 1 to 4 carbon atoms.

42. The method of claim 31 wherein $R_2'$ is 1-methyl-1H-imidazolyl.

43. The method of claim 31 wherein $R_2'$ is tetrazolyl optionally substituted with alkyl of 1 to 4 carbon atoms.

44. The method of claim 31 wherein the compound is selected from the group consisting of 2,8-bis-(trifluoromethyl)-4-hydroxy-N-(oxazol-2-yl)-3-quinoline-carboxamide, 2,8-bis-(trifluoromethyl)-4-hydroxy-N-(5-methyl-isoxazol-3-yl)-3-quinoline-carboxamide, 2,8-bis-(trifluoromethyl)-4-hydroxy-N-(2-pyridinyl)-3-quinoline-carboxamide, 2,8-bis-(trifluoromethyl)-4-hydroxy-N-(1-methyl-1H-imidazol-2-yl)-3-quinolinecarboxamide, 2,8-bis-(trifluoromethyl)-4-hydroxy-N-(1H-tetrazol-5-yl)-3-quinoline-carboxamide, 2,7-bis-(trifluoromethyl)-4-hydroxy-N-(2-thiazolyl)-3-quinoline-carboxamide, 2-trifluoromethyl-4-hydroxy-N-(2-thiazolyl)-3-quinoline-carboxamide, 2-trifluoromethyl-6-isopropyl-4-hydroxy-N-(2-thiazolyl)-3-quinoline-carboxamide, 2-trifluoromethyl-6-methoxy-4-hydroxy-N-(2-thiazolyl)-3-quinoline-carboxamide and their non-toxic, pharmaceutically acceptable acid addition salts.

45. The method of claim 31 wherein the compound is 2,8-bis-(trifluoromethyl)-4-hydroxy-N-(2-thiazolyl)-3-quinoline-carboxamide.

* * * * *

UNITED STATES PATENT AND TRADEMARK OFFICE
CERTIFICATE OF CORRECTION

PATENT NO. : 4,299,831
DATED : November 10, 1981
INVENTOR(S) : FRANÇOIS CLÉMENCE ET AL.

It is certified that error appears in the above—identified patent and that said Letters Patent is hereby corrected as shown below:

Column 5, line 41: "the" should read -- The --.

Column 7, line 63; column 10, line 52: Delete "e".

Column 7, line 64; column 10, line 53: "thylidene" should read -- ethylidene --.

Column 11, line 47: "-trifluoro-(3-" should read -- -trifluoro-1-(3- --.

Column 11, line 59: "3.36 g" should read -- 3.35 g --.

Column 12, line 38: "0.1" should read -- 0.01 --.

Signed and Sealed this

Twentieth Day of April 1982

[SEAL]

Attest:

GERALD J. MOSSINGHOFF

*Attesting Officer*     *Commissioner of Patents and Trademarks*